(12) United States Patent
Pouget et al.

(10) Patent No.: US 9,475,829 B2
(45) Date of Patent: Oct. 25, 2016

(54) METHOD FOR THE HYDROSILYLATION OF A SILOXANE PHOTOCATALYSED BY A POLYOXOMETALATE COMPOUND

(71) Applicant: BLUESTAR SILICONES FRANCE SAS, Lyons (FR)

(72) Inventors: Emmanuel Pouget, Lyons (FR); Jean-Marc Frances, Meyzieu (FR)

(73) Assignee: BLUESTAR SILICONES FRANCE SAS, Lyon (FR)

( * ) Notice: Subject to any disclaimer, the term of this patent is extended or adjusted under 35 U.S.C. 154(b) by 0 days.

(21) Appl. No.: 14/654,014

(22) PCT Filed: Dec. 19, 2013

(86) PCT No.: PCT/FR2013/053190
§ 371 (c)(1),
(2) Date: Jun. 19, 2015

(87) PCT Pub. No.: WO2014/096720
PCT Pub. Date: Jun. 26, 2014

(65) Prior Publication Data
US 2015/0315214 A1    Nov. 5, 2015

(30) Foreign Application Priority Data

Dec. 21, 2012  (FR) ..................................... 12 62594

(51) Int. Cl.
*C07F 7/08* (2006.01)
*B01J 31/34* (2006.01)
*B01J 35/00* (2006.01)

(52) U.S. Cl.
CPC .............. *C07F 7/0852* (2013.01); *B01J 31/34* (2013.01); *B01J 35/004* (2013.01); *C07F 7/0879* (2013.01)

(58) Field of Classification Search
CPC ..... C07F 7/0852; C07F 7/0879; B01J 31/34; B01J 35/004
USPC .......................................................... 556/439
See application file for complete search history.

(56) References Cited

U.S. PATENT DOCUMENTS 3,775,452 A    11/1973  Karstedt et al.
7,858,814 B2 *  12/2010  Kortz .................... B01J 23/002
                                                    502/207

FOREIGN PATENT DOCUMENTS

WO        2011006044 A2    1/2011

OTHER PUBLICATIONS

International Search Report from corresponding PCT/FR2013/053190, mailed Feb. 17, 2014.
Lalevee, "Decatungstate Silane: A New and Promising Radical Source Under Soft Light Irradiation", Jun. 1, 2011.
Tzirakis et al. "Decatungstate as an efficient photocatalyst in organic chemistry", Jan. 1, 2009.
De Vekki, "Hydrosilylation on photoactivated catalysts", Aug. 18, 2011.

* cited by examiner

*Primary Examiner* — Porfirio Nazario Gonzalez
(74) *Attorney, Agent, or Firm* — McBee Moore Woodward Vanik IP LLC (57) ABSTRACT

The invention concerns a method of hydrosilylation between a siloxane compound (A) comprising at least one hydrogen atom bonded to a silicon atom and an unsaturated compound (B) comprising at least one alkene function and/or at least one alkyne function, the method being characterized in that it is catalyzed by a photocatalyst selected from among the polyoxometalates.

19 Claims, 1 Drawing Sheet

METHOD FOR THE HYDROSILYLATION OF A SILOXANE PHOTOCATALYSED BY A POLYOXOMETALATE COMPOUND

CROSS REFERENCE TO RELATED APPLICATIONS

This application is a §371 National Stage Application of PCT/FR2013/053190, filed 19 Dec. 2013, which claims priority to FR 1262594, filed 21 Dec. 2012.

BACKGROUND

1. Field of the Invention

The invention lies in the technical field of siloxanes, and in particular of polyorganosiloxanes also commonly known as silicones. More specifically, the present invention relates to hydrosilylation reactions, also known as polyadditions, of an unsaturated compound with a siloxane comprising at least one hydrogen atom bonded to a silicon atom.

2. Description of Related Art

In the field of silicones, hydrosilylation is a major reaction.

During a hydrosilylation reaction, a compound comprising at least one unsaturation reacts with a compound comprising at least one hydrogen atom bonded to a silicon atom. This reaction can, for example, be described by the reaction equation (1) in the case of an unsaturation of alkene type:

(1)

or by the reaction equation (2) in the case of an unsaturation of alkyne type:

(2)

Hydrosilylation therefore makes it possible to bond siloxanes, and in particular silicones, comprising Si—H units, with compounds that have at least one unsaturation of alkene or alkyne type, for example silicones comprising Si-vinyl units.

Hydrosilylation reactions are conventionally carried out by catalysis. Typically, the catalyst appropriate for this reaction is a platinum catalyst, such as, for example, chloroplatinic acid hexahydrate or the Karstedt catalyst which consists of platinum complexes with divinyltetramethyldisiloxane as ligand (see, for example, in U.S. Pat. No. 3,775,452).

However, the use of a platinum catalyst is problematic. It is in fact preferable to avoid the use of platinum on an industrial scale since it is an expensive metal which is becoming increasingly scarce and the cost of which fluctuates enormously. As a result, the cost of siliceous compounds produced by hydrosilylation, such as siloxanes and polyorganosiloxanes functionalized by hydrosilylation and silicone compositions crosslinkable by hydrosilylation, is indexed to the cost of platinum, which is worrying both for manufacturers and for their clients.

It would therefore be advantageous to have an alternative to the platinum-catalyzed hydrosilylation reaction. It would be quite particularly advantageous to provide a novel type of catalyst for siloxane hydrosilylation reactions not containing platinum.

The use of other catalysts has been proposed in the past, for example the use of rhodium or iridium. However, these metals are as rare as platinum, and the use thereof does not solve the problems mentioned. International patent application WO 2011/006044 describes the use of complexes of manganese, of iron, of cobalt or of nickel containing pyridine diimine ligands as hydrosilylation catalyst. In addition, the publication by D. A. de Vekki ("Hydrosilylation on Photoactivated Catalyst", *Russian Journal of General Chemistry*, 2011, 81, 7, 1480-1492) describes photoactivatable catalysts for hydrosilylation of C=C, C≡C and C=O bonds.

One of the objectives of the present invention is therefore to provide a process for hydrosilylation between a siloxane compound and an unsaturated compound, which would use an advantageously inexpensive catalyst, which is easy to supply, which is easy to handle and/or which has a low toxicity or is non-toxic. In addition, it is desirable for the hydrosilylation yields obtained with this alternative catalyst to be as high as possible.

Moreover, the use of compounds of the polyoxometalate family, commonly called POMs, as a catalyst has been described in the literature. POMs are anionic clusters of transition metal oxides. The publication by D. Tzirakis et al. "Decatungstate as an efficient photocatalyst in organic chemistry" (*Chemical Society Reviews*, 2009, 38, 2609-2621) describes in particular the photochemical properties of POMs, and in particular of decatungstate, and the use thereof as a photocatalyst. This publication describes the use of decatungstate for the creation of carbon-carbon bonds by homolytic breaking of carbon-hydrogen bonds, for oxidation in the presence of oxygen and for degradation of organic pollutants.

More recently, the researchers Jacques Lalevée, Nicolas Blanchard, Mohamad-Ali Tehfe and Jean Pierre Fouassier have described, for the first time, in a publication entitled "Decatungstate ($W_{10}O_{32}^{4-}$)/Silane: a New and Promising Radical Source Under Soft Light Irradiation" (*Macromolecular Rapid Communications*, 2011, 32, 838-843), that decatungstate can be used as a photocatalyst for forming silyl radicals from silanes. The photopolymerization of epoxides has been presented as a concrete use of this property.

However, no application in hydrosilylation has been envisioned. In addition, these disclosures do not concern siloxanes, the reactivity of which is different than that of silanes.

SUMMARY

The invention relates firstly to a process for hydrosilylation between a siloxane compound (A) comprising at least one hydrogen atom bonded to a silicon atom and an unsaturated compound (B) comprising at least one alkene function and/or at least one alkyne function, said process being characterized in that it is catalyzed by a photocatalyst chosen from polyoxometalates.

A subject of the present invention is also a composition comprising:

a siloxane compound (A) comprising at least one hydrogen atom bonded to a silicon atom, an unsaturated compound (B) comprising at least one alkene function and/or at least one alkyne function, and a photocatalyst chosen from polyoxometalates.

Finally, the use of a polyoxometalate, preferably of a decatungstate, as photocatalyst of a reaction for hydrosilylation of an unsaturated compound comprising at least one alkene function and/or at least one alkyne function, with a siloxane compound comprising at least one hydrogen atom bonded to a silicon atom, is also a subject of the present invention.

DETAILED DESCRIPTION OF A PREFERRED EMBODIMENT

It is specified that, throughout this description, the expression "between . . . and . . . " should be understood to include the limits mentioned.

The present invention therefore relates to a hydrosilylation reaction between, on the one hand, a siloxane compound (A) comprising at least one hydrogen atom bonded to a silicon atom and, on the other hand, an unsaturated compound (B), this reaction being photocatalyzed by a polyoxometalate, commonly known as POM.

As previously explained, POMs have already been described in the literature. POMs are anionic clusters consisting of at least 3 transition metal oxoanions which share their oxygen atoms, and together form a structured three-dimensional network.

The POMs can be described by the general formula $[X_aM_bO_c]^{n-}$ in which

X represents a hydrogen atom or an atom chosen from B, Al, Si, P, S, Ga, Ge, As, Ce, Th and Sb;

M represents a transition metal;

O represents an oxygen atom;

a represents an integer which can be 0, 1 or 2;

b represents an integer which can be from 3 to 20;

c represents an integer which can be from 6 to 62; and n represents an integer greater than or equal to 1, preferably which can be from 1 to 10.

This general formula also includes the hydrated forms of the anionic clusters, although said forms are not explicitly represented.

In this general formula, all the atoms represented by M, and optionally all the atoms represented by X if a is 2, may be identical or different.

A POM thus contains transition metals M. The transition metal of the POM can be chosen from the elements of groups 4, 5, 6 and 7 of the periodic table, preferably from the elements of groups 5 and 6. The transition metal can preferably be chosen from the group consisting of vanadium (V), niobium (Nb), tantalum (Ta), chromium (Cr), molybdenum (Mo) and tungsten (W), more preferably from the group consisting of vanadium (V), niobium (Nb), tantalum (Ta), molybdenum (Mo) and tungsten (W), even more preferably from the group consisting of vanadium (V), molybdenum (Mo) and tungsten (W). In the case where the POM is based on vanadium, the term polyoxovanadate can be used. In the case where the POM is based on molybdenum, the term polyoxomolybdate can be used. In the case where the POM is based on tungsten, the term polyoxotungstate can be used. The POM used in the present invention can be a polyoxovanadate, a polyoxomolybdate, a polyoxotungstate, or mixtures thereof, and quite particularly a polyoxotungstate. Polyoxotungstates are, for example, described in the reference work "*Advanced Inorganic Chemistry: a comprehensive text*" by Cotton and Wilkinson.

The transition metal in the POM is generally in a high oxidation state, preferably V or VI.

According to one embodiment, the POM may consist only of transition metal and oxygen atoms, which corresponds to the fact that the symbol a is zero in the general formula $[X_aM_bO_c]^{n-}$. In this embodiment, the general formula of the POM is then $[M_bO_c]^{n-}$, in which M, O, b, c and n have the meanings described above. This type of POM can be denoted using the term "isopolyanion".

However, it is possible, in another embodiment, for the POM to also comprise one or more heteroatoms, which corresponds to the fact that the symbol a is other than zero in the general formula $[X_aM_bO_c]^{n-}$. X is preferably chosen from the group consisting of phosphorus (P) and silicon (Si). This type of POM can be denoted using the term "heteropolyanion".

The values of the symbols a, b, c and n are such that the rules of valence of the various atoms are adhered to so as to obtain an anionic cluster.

The POM used in the present invention can be chosen from the group consisting of $[W_{10}O_{32}]^{4-}$, $[Mo_6O_{19}]^{2-}$, $[V_{10}O_{28}]^{6-}$, $[PW_{12}O_{40}]^{3-}$, $[PMo_{12}O_{40}]^{3-}$, $[SiW_{10}O_{40}]^{4-}$ and mixtures thereof. Preferably, the POM used in the present invention is chosen from POMs not containing phosphorus. Quite particularly preferably, the POM used in the present invention is $[W_{10}O_{32}]^{4-}$, commonly known as "decatungstate".

Since POMs are ionic compounds, they can be present in salt form. The counterion(s) can be chosen from the group consisting of the proton ($H^+$), of alkali metal ions, in particular $Na^+$, $K^+$ and $Li^+$, of halogenated cations, in particular iodonium, and of ammonium cations, sulfonium cations, phosphonium cations, ferrocenium cations and carbocations.

The photocatalyst used in the process which is the subject of the invention can be a decatungstate salt. It is very preferably tetrabutylammonium decatungstate (TBADT), of formula $(n-Bu_4N^+)_4 [W_{10}O_{32}]^{4-}$.

The POMs can be synthesized according to the processes described in the prior art. For example, the synthesis of TBADT has been described in the publication by Protti et al. (*Chem. Commun.*, 2009, 7351-7353) and in the publication by Chemseddine et al. (*Inorg. Chem.*, 1984, 23, 2609). This synthesis can be carried out using sodium tungstate and tetrabutylammonium bromide in an acidic medium.

Figure 1:
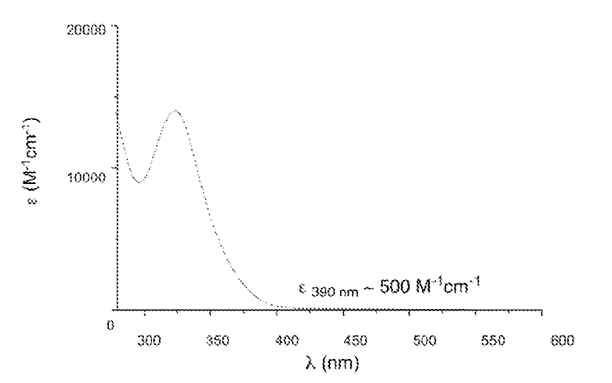
FIG. 1 represents the absorption spectrum of decatungstate in solution in acetonitrile.

The POMs in general, and the decatungstate in particular, are advantageous because of their photochemical properties. They can in fact be excited under very mild irradiation conditions, under near-UV or even under visible light. FIG. 1 shows the absorption spectrum of the decatungstate in acetonitrile. It is noted that this photocatalyst absorbs light in wavelengths between approximately 300 nm and approximately 420 nm. The maximum absorption in acetonitrile of the decatungstate is centered around approximately 324 nm. The absorption of this compound in the visible range is significant: the molar extinction coefficient at 400 nm ($\epsilon_{400\ nm}$) is approximately 400 $l \cdot mol^{-1} \cdot cm^{-1}$ and the molar extinction coefficient at 390 nm ($\epsilon_{390\ nm}$) is approximately 500 $l \cdot mol^{-1} \cdot cm^{-1}$. It is therefore possible to excite it in this wavelength range. The photocatalyst thus excited is then capable of carrying out an abstraction of hydrogen on a siloxane compound which has a hydrogen atom bonded to a silicon atom.

Since the POM catalyst is active only when it is irradiated, it is easy to stop the hydrosilylation reaction by stopping the irradiation. This represents an advantage compared with the catalysts used in the prior art, with which it is difficult to control or stop the reaction once the latter has been initiated. One of the advantages of the present invention therefore lies in the fact that the progression of the reaction is controllable. The hydrosilylation reaction is thus safer from an industrial risk point of view.

One of the reagents of the hydrosilylation reaction according to the invention is a siloxane compound (A) comprising at least one hydrogen atom bonded to a silicon atom.

In the present invention, the term "siloxane" compound is intended to mean chemical compounds which have at least one ≡Si—O—Si≡ unit. Silane compounds do not belong to the siloxane compound group.

Any siloxane compound comprising at least one hydrogen atom bonded to a silicon atom can be used in the process according to the invention, in so far as it does not contain a reactive chemical function which can hinder, or even prevent, the hydrosilylation reaction.

The siloxane compound (A) comprises at least two silicon atoms, preferably at least 3 silicon atoms or more.

Said siloxane compound (A) can advantageously be a polyorganosiloxane comprising at least one unit of formula (I):

$$H_d Z_e SiO_{(4-(d+e))/2} \qquad (I)$$

in which:
Z represents a monovalent radical other than a hydrogen atom,
d and e represent integers, d being 1 or 2, e being 0, 1 or 2 and (d+e) being 1, 2 or 3;
and optionally other units of formula (II):

$$Z_f SiO_{(4-f)/2} \qquad (II)$$

in which:
Z has the same meaning as above, and
f represents an integer between 0 and 3.

It is understood, in formula (I) and in formula (II) above, that, if several Z groups are present, they may be identical to or different than one another.

In formula (I), the symbol d may preferentially be 1.

Furthermore, in formula (I) and in formula (II), Z may represent a monovalent radical chosen from the group consisting of an alkyl group having 1 to 8 carbon atoms, which is optionally substituted with at least one halogen atom, and an aryl group. Z may advantageously represent a monovalent radical chosen from the group consisting of methyl, ethyl, propyl, 3,3,3-trifluoropropyl, xylyl, tolyl and phenyl. Examples of units of formula (I) are the following: $H(CH_3)_2SiO_{1/2}$, $HCH_3SiO_{2/2}$ and $H(C_6H_5)SiO_{2/2}$.

Said siloxane compound (A) may advantageously be a polyorganosiloxane comprising at least two units of formula (I) or more.

The polyorganosiloxane may have a linear, branched, cyclic or network structure.

When it is a question of linear polyorganosiloxanes, they may essentially consist:
of siloxyl units "D" chosen from units of formulae $HZSiO_{2/2}$ and $Z_2SiO_{2/2}$;
of siloxyl units "M" chosen from units of formulae $HZ_2SiO_2$ and $Z_3SiO_{2/2}$.

These linear polyorganosiloxanes may be oils having a dynamic viscosity at 25° C. of between 1 mPa·s and 100 000 mPa·s, preferentially between 10 mPa·s and 5000 mPa·s, or gums having a dynamic viscosity at 25° C. greater than 100 000 mPa·s.

When it is a question of cyclic polyorganosiloxanes, they may consist of siloxyl units "D" chosen from units of formulae $HZSiO_{2/2}$ and $Z_2SiO_{2/2}$, or of siloxyl units of formula $HZSiO_{2/2}$ only. The units of formula $Z_2SiO_{2/2}$ may in particular be dialkylsiloxy or alkylarylsiloxy. These cyclic polyorganosiloxanes may have a dynamic viscosity at 25° C. of between 1 mPa·s and 5000 mPa·s.

The dynamic viscosity at 25° C. of all the polymers described in the present application can be measured using a Brookfield viscometer, according to standard AFNOR NFT 76 102 of February 1972.

Examples of polyorganosiloxanes which may be siloxane compounds (A) are:
dimethylpolysiloxanes comprising hydrodimethylsilyl ends;
dimethylhydromethylpolysiloxanes comprising trimethylsilyl ends;
dimethylhydromethylpolysiloxanes comprising hydrodimethylsilyl ends;
hydromethylpolysiloxanes comprising trimethylsilyl ends;
cyclic hydromethylpolysiloxanes.

When it is a question of branched or network polyorganosiloxanes, they may also comprise:
siloxyl units "T" chosen from units of formulae $HSiO_{3/2}$ and $ZSiO_{3/2}$;
siloxyl units "Q" of formula $SiO_{4/2}$.

An example of a polyorganosiloxane which can be a siloxane compound (A) is the compound having the formula below:

The second of the reagents of the hydrosilylation reaction according to the invention is an unsaturated compound.

The unsaturated compound (B) according to the invention is a chemical compound comprising at least one unsaturation which is not part of an aromatic ring. The unsaturated compound (B) comprises at least one alkene function and/or one alkyne function. Any compound comprising at least one alkene function and/or one alkyne function can be used in the process according to the invention, in so far as it does not contain a reactive chemical function which can hinder, or even prevent, the hydrosilylation reaction.

According to one embodiment, the unsaturated compound (B) comprises one or more alkene functions and from 2 to 40 carbon atoms. It may also comprise 1 to 3 heteroatoms chosen from N, O, F, Cl, Br and I. When the unsaturated compound (B) comprises several alkene functions, said functions may or may not be conjugated.

According to another embodiment, the unsaturated compound (B) comprises one or more alkyne functions, and 2 to 40 carbon atoms. It may also comprise 1 to 3 heteroatoms chosen from N, O, F, Cl, Br and I. When the unsaturated compound (B) comprises several alkyne functions, said functions may or may not be conjugated.

Said unsaturated compound (B) can be chosen from the group consisting of:
- non-polymeric unsaturated organic compounds,
- polyorganosiloxane compounds comprising at least one alkene function and/or at least one alkyne function, and mixtures thereof.

In the case where the unsaturated compound (B) is chosen from non-polymeric unsaturated organic compounds, it can generally be chosen from the compounds of formula (III) or (IV):

(III)

(IV)

in which $R^1$, $R^2$, $R^3$ and $R^4$ represent, independently of one another, a monovalent radical.

$R^1$, $R^2$, $R^3$ and $R^4$ can be chosen, independently of one another, from the group consisting of:
- a hydrogen atom,
- a halogen atom chosen from fluorine, chlorine, bromine and iodine,
- an alkyl group,
- a cycloalkyl group,
- an aryl group,
- a heteroaryl group,
- a heterocycloalkyl group,
- an alkoxy group,
- an aryloxy group,
- a cycloalkoxy group,
- an alkylsilyl group,
- an alkoxysilyl group,
- a carboxylic acid group,
- an alkyl ester group,
- a urea group,
- an amide group,
- a sulfonamide group,
- an imide group,
- a cyano group,
- an aldehyde group,
- an alcohol group,
- a thiol group,
- an amine group,
- an imine group,
- a sulfide group,
- a sulfoxide group,
- a sulfone group,
- or an azide group;

it being possible for these groups to themselves be substituted on their alkyl and/or cycloalkyl and/or aryl part(s) with one or more optionally halogenated $C_1$ to $C_8$ alkyl groups, with one or more optionally halogenated $C_1$ to $C_8$ alkoxy groups, with one or more optionally halogenated aryl groups, with one or more groups optionally halogenated cycloalkyl groups, with one or more optionally halogenated heteroaryl groups, with one or more optionally halogenated heterocycloalkyl groups, with one or more halogen atoms, with one or more carboxylic acid groups, with one or more ester groups, with one or more ether groups, with one or more urea groups, with one or more amide groups, with one or more sulfonamide groups, with one or more imide groups, with one or more cyano groups, with one or more aldehyde groups, with one or more ketone functions, with one or more alcohol groups, with one or more thiol groups, with one or more amine groups, with one or more imine groups, with one or more sulfide groups, with one or more sulfoxide groups, with one or more sulfone groups, and/or with one or more azide groups;

or else at least two groups chosen from $R^1$, $R^2$, $R^3$ and $R^4$ form, together with the carbon atoms to which they are bonded, one or more cycloalkyl, heterocycloalkyl, aryl or heteroaryl groups, it being possible for these cycloalkyl, heterocycloalkyl, aryl and heteroaryl groups to be substituted with one or more optionally halogenated $C_1$ to $C_8$ alkyl groups, with one or more optionally halogenated $C_1$ to $C_8$ alkoxy groups, with one or more optionally halogenated aryl groups, with one or more halogen atoms, with one or more carboxylic acid groups, with one or more ester groups, with one or more ether groups, with one or more urea groups, with one or more amide groups, with one or more sulfonamide groups, with one or more imide groups, with one or more cyano groups, with one or more aldehyde groups, with one or more ketone functions, with one or more alcohol groups, with one or more thiol groups, with one or more amine groups, with one or more imine groups, with one or more sulfide groups, with one or more sulfoxide groups, with one or more sulfone groups, and/or with one or more azide groups; the remaining groups being as previously defined.

According to the invention, the term "alkyl" is intended to mean a linear or branched, saturated hydrocarbon-based chain containing from 1 to 20 carbon atoms, preferably from 1 to 8 carbon atoms. An alkyl group may be chosen from the group consisting of methyl, ethyl, isopropyl, n-propyl, tert-butyl, isobutyl, n-butyl, n-pentyl, isoamyl and 1,1-dimethylpropyl.

According to the invention, the term "cycloalkyl" is intended to mean a monocyclic or polycyclic, preferably monocyclic or bicyclic, saturated hydrocarbon-based group containing from 3 to 20 carbon atoms, preferably from 5 to 8 carbon atoms. When the cycloalkyl group is polycyclic, the multiple cyclic nuclei may be attached to one another via a covalent bond and/or via a spiran atom and/or be condensed with one another. A cycloalkyl group may be chosen from the group consisting of cyclopropyl, cyclobutyl, cyclopentyl, cyclohexyl, cycloheptyl, cyclooctyl, adamantane and norborane.

According to the invention, the term "aryl" is intended to mean a monocyclic or polycyclic aromatic hydrocarbon-based group containing from 5 to 18 carbon atoms. An aryl group may be chosen from the group consisting of phenyl, naphthyl, anthracenyl and phenanthryl.

According to the invention, the term "halogen atom" is intended to mean an atom chosen from the group consisting of fluorine, chlorine, bromine and iodine.

According to the invention, the term "heteroaryl" is intended to mean an aryl group, i.e. a monocyclic or polycyclic aromatic hydrocarbon-based group containing from 5 to 18 carbon atoms, in which at least one carbon atom has been replaced with a heteroatom chosen from O, N, S and P. A heteroaryl group may be chosen from the group consisting of pyranyl, furanyl, pyridinyl, pyrimidinyl, pyrrolyl, pyrazolyl, imidazolyl, isothiazolyl, isoxazolyl and indolyl.

According to the invention, the term "heterocycloalkyl" is intended to mean a cycloalkyl group, i.e. a monocyclic or polycyclic, preferably monocyclic or bicyclic, saturated hydrocarbon-based group containing from 3 to 20 carbon atoms, in which at least one carbon atom has been replaced with a heteroatom chosen from O, N, S and P. A heterocycloalkyl group may in particular be the oxiranyl monocyclic group or the epoxycyclohexyl bicyclic group.

According to the invention, the term "alkoxy" is intended to mean an alkyl group as defined above, bonded to an oxygen atom. An alkoxy group may be chosen from the group consisting of methoxy, ethoxy, propoxy and butoxy.

According to the invention, the term "aryloxy" is intended to mean an aryl group as defined above, bonded to an oxygen atom. An aryloxy group may, for example, be the phenoxy group.

According to the invention, the term "cycloalkoxy" is intended to mean a cycloalkyl group as defined above, bonded to an oxygen atom.

According to the invention, the term "alkylsilyl" is intended to mean an alkyl group as defined above, bonded to a silicon atom.

According to the invention, the term "alkoxysilyl" is intended to mean an alkoxy group as defined above, bonded to a silicon atom.

Preferably, $R^1$, $R^2$, $R^3$ and $R^4$ represent, independently of one another:
  a hydrogen atom;
  a $C_1$ to $C_8$ alkyl group, optionally substituted with a hydroxyl group and/or with a halogen atom;
  a phenyl, optionally substituted with a $C_1$ to $C_4$ alkyl group, with a halogen, with a $C_1$ to $C_4$ alkyl group itself substituted with one or more halogens, with a $C_1$ to $C_4$ alkoxy group or with an amine function optionally substituted once or twice with a $C_1$ to $C_4$ alkyl group;
  a pyridine;
  a $C_1$ to $C_8$ alkyl ester;
  a cyano function;
  a carboxylic acid function;
  a $C_1$ to $C_4$ acyloxy group, in particular acetyloxy group;
  a primary amide group, which is in particular unsubstituted on the nitrogen or substituted once or twice with a $C_1$ to $C_4$ alkyl group;
  a polyethoxylated alkyl group, optionally substituted with a hydroxyl or a ketone;
  an epoxycyclohexyl group;
  an oxiranyl group or a $C_1$ to $C_8$ alkyl group substituted with an oxiranyl group.

Advantageously, $R^1$ may be a hydrogen atom, and $R^2$ may represent a substituent other than a hydrogen atom. In the case of a compound of formula (III), $R^3$ and $R^4$ may also be hydrogen atoms.

Said unsaturated compound (B) may also be a non-polymeric unsaturated organic compound chosen from the group consisting of:
  acetylene;
  $C_1$ to $C_4$ alkyl acrylates and methacrylates;
  acrylic or methacrylic acid;
  alkenes, preferably octene and more preferentially 1-octene;
  allyl alcohol;
  allylamine;
  allyl glycidyl ether;
  piperidine allyl ether, preferentially sterically hindered piperidine allyl ether;
  styrenes, preferentially alpha-methylstyrene;
  1,2-epoxy-4-vinylcyclohexane;
  allyl chloride;
  chloroalkenes, preferably allyl chloride; and
  fluoroalkenes, preferably 4,4,5,5,6,6,7,7,7-nonafluoro-1-heptene.

The unsaturated compound (B) may also be chosen from compounds comprising several alkene functions, preferably two or three alkene functions, and particularly preferably chosen from the following compounds:

with p being 1 or 2, and with q being from 2 to 6, preferably q being 2 or 4.

The hydrosilylation process according to the invention makes it possible, according to this embodiment, to bond organic groups advantageously comprising an advantageous chemical function to siloxanes, in particular to polyorganosiloxanes. When the unsaturated compound (B) comprises a single alkene or alkyne function, the process according to the invention may be used as a process for functionalization which may be total or partial. When the unsaturated compound (B) comprises two alkene or alkyne functions, or more, it acts as a bridge between several siloxane compounds (A), preferably between several polysiloxanes.

In the case where the unsaturated compound (B) is chosen from polyorganosiloxane compounds comprising at least one alkene function and/or at least one alkyne function, it may be chosen, generally, from the polyorganosiloxanes comprising at least one unit of formula (V):

$$Y_g L_h SiO_{(4-(g+h))/2} \quad (V)$$

in which:
  Y represents a linear or branched radical containing between 2 and 12 carbon atoms, having at least one alkene function and/or at least one alkyne function, and optionally at least one heteroatom;
  L represents a monovalent radical not comprising an alkene or alkyne function;
  g and h represent integers, g being 1, 2 or 3, h being 0, 1 or 2 and (g+h) being 1, 2 or 3;
and optionally comprising other units of formula (VI):

$$L_i SiO_{(4-i)/2} \quad (VI)$$

in which:
  L has the same meaning as above, and
  i represents an integer between 0 and 3.

It is understood in formula (V) and in formula (VI) above that, if several Y and L groups are present, they may be identical to or different than one another.

In formula (V), the symbol g may preferentially be 1 or 2, more preferentially 1.

Furthermore, in formula (V) and in formula (VI), L may represent a monovalent radical chosen from the group consisting of an alkyl group having 1 to 8 carbon atoms, which is optionally substituted with at least one halogen atom, and an aryl group. L may advantageously represent a monovalent radical chosen from the group consisting of methyl, ethyl, propyl, 3,3,3-trifluoropropyl, xylyl, tolyl and phenyl.

In addition, in formula (V) and in formula (VI), the alkene function and/or the alkyne function in the Y radical may be advantageously at the end of a chain. Y may advantageously represent a radical chosen from the group consisting of vinyl, propenyl, 3-butenyl, 5-hexenyl, 9-decenyl, 10-undecenyl, 5,9-decadienyl and 6,11-dodecadienyl.

Preferably, the unsaturated compound (B) is chosen from polyorganosiloxanes comprising at least two units of formula (V) or more.

The polyorganosiloxane may have a linear, branched, cyclic or network structure.

When it is a question of linear polyorganosiloxanes, they may essentially consist:
of siloxyl units "D" chosen from units of formulae $Y_2SiO_{2/2}$, $YLSiO_{2/2}$ and $L_2SiO_{2/2}$;
of siloxyl units "M" chosen from units of formulae $Y_3SiO_{1/2}$, $Y_2LSiO_{1/2}$, $YL_2SiO_{1/2}$ and $L_3SiO_{2/2}$.

By way of examples of units "D", mention may be made of dimethylsiloxy, methylphenylsiloxy, methylvinylsiloxy, methylbutenylsiloxy, methylhexenylsiloxy, methyldecenylsiloxy and methyldecadienylsiloxy groups.

By way of example of units "M", mention may be made of trimethylsiloxy, dimethylphenylsiloxy, dimethylvinylsiloxy and dimethylhexenylsiloxy groups.

These linear polyorganosiloxanes may be oils having a dynamic viscosity at 25° C. of between 1 mPa·s and 100 000 mPa·s, preferentially between 10 mPa·s and 5000 mPa·s, or gums having a dynamic viscosity at 25° C. greater than 100 000 mPa·s.

When it is a question of cyclic polyorganosiloxanes, they may consist of siloxyl units "D" chosen from units of formulae $Y_2SiO_{2/2}$, $YLSiO_{2/2}$ and $L_2SiO_{2/2}$. Examples of such units "D" are described above. The cyclic polyorganosiloxanes may have a dynamic viscosity at 25° C. of between 1 mPa·s and 5000 mPa·s.

The dynamic viscosity at 25° C. of all the polymers described in the present application can be measured using a Brookfield viscometer, according to standard AFNOR NFT 76 102 of February 1972.

Examples of polyorganosiloxanes which may be unsaturated compounds (B) are:
dimethylpolysiloxanes comprising dimethylvinylsilyl ends;
dimethylphenylmethylpolysiloxanes comprising dimethylvinylsilyl ends;
dimethylvinylmethylpolysiloxanes comprising dimethylvinylsilyl ends;
dimethylvinylmethylpolysiloxanes comprising trimethylsilyl ends;
cyclic methylvinylpolysiloxanes.

The hydrosilylation process according to the invention makes it possible, according to this embodiment, to bond siloxane compounds (A), preferentially polysiloxanes having at least one hydrogen atom bonded to a silicon atom, with polysiloxanes having at least one alkene function or one alkyne function. The process according to the invention can be used as a crosslinking process. In this case, it is preferable for the polysiloxanes used as siloxane compounds (A) to comprise, per molecule, at least three hydrogen atoms bonded to silicon atoms, and for the polysiloxanes used as unsaturated compound (B) to comprise, per molecule, at least two unsaturated functions chosen from alkene or alkyne functions.

According to one particular embodiment of the present invention, it is possible for the siloxane compound (A) comprising at least one hydrogen atom bonded to a silicon atom and the unsaturated compound (B) comprising at least one alkene function and/or at least one alkyne function to be one and the same compound.

This compound may be described as "bifunctional" since it then comprises, on the one hand, at least one alkene function and/or at least one alkyne function and, on the other hand, at least one silicon atom and at least one hydrogen atom bonded to the silicon atom. It is capable of reacting with itself by means of a hydrosilylation reaction.

The invention can thus also relate to a process for hydrosilylation of a bifunctional compound with itself, said bifunctional compound comprising, on the one hand, at least one alkene function and/or at least one alkyne function and, on the other hand, at least one silicon atom and at least one hydrogen atom bonded to the silicon atom, said process being characterized in that it is catalyzed by a photocatalyst chosen from polyoxometalates.

Said bifunctional compound may advantageously be a polyorganosiloxane comprising at least one unit of formula (I):

$$H_d Z_e SiO_{(4-(d+e))/2} \qquad (I)$$

in which:
Z represents a monovalent radical other than a hydrogen atom;
d and e represent integers, d being 1 or 2, e being 0, 1 or 2 and (d+e) being 1, 2 or 3;
and at least one unit of formula (V):

$$Y_g L_h SiO_{(4-(g+h))/2} \qquad (V)$$

in which:
Y represents a linear or branched radical containing between 2 and 12 carbon atoms, having at least one alkene function and/or at least one alkyne function, and optionally at least one heteroatom,
L represents a monovalent radical not comprising an alkene or alkyne function,
g and h represent integers, g being 1, 2 or 3, h being 0, 1 or 2 and (g+h) being 1, 2 or 3;
and optionally other units of formula (VII):

$$W_j SiO_{(4-j)/2} \qquad (VII)$$

in which:
W represents a monovalent radical other than a hydrogen atom and not comprising an alkene or alkyne function, and
j represents an integer between 0 and 3.

It is understood in formula (I), in formula (V) and in formula (VII) above that, if several Z, Y, L and W groups are present, they may be identical to or different than one another.

In formula (I), the symbol d may preferentially be 1.

Furthermore, in formula (I), Z may represent a monovalent radical chosen from the group consisting of an alkyl group having 1 to 8 carbon atoms, which is optionally substituted with at least one halogen atom, and an aryl group. Z may advantageously represent a monovalent radical chosen from the group consisting of methyl, ethyl, propyl, 3,3,3-trifluoropropyl, xylyl, tolyl and phenyl. Examples of units of formula (I) are the following: $H(CH_3)_2SiO_{1/2}$, $HCH_3SiO_{2/2}$ and $H(C_6H_5)SiO_{2/2}$.

In formula (V), the symbol g may preferentially be 1 or 2, more preferentially 1.

Furthermore, in formula (V), L may represent a monovalent radical chosen from the group consisting of an alkyl group having 1 to 8 carbon atoms, which is optionally substituted with at least one halogen atom, and an aryl group. L may advantageously represent a monovalent radical chosen from the group consisting of methyl, ethyl, propyl, 3,3,3-trifluoropropyl, xylyl, tolyl and phenyl.

In addition, in formula (V), the alkene function and/or the alkyne function in the Y radical may be advantageously at the end of the chain. Y may advantageously represent a radical chosen from the group consisting of vinyl, propenyl, 3-butenyl, 5-hexenyl, 9-decenyl, 10-undecenyl, 5,9-decadienyl and 6,11-dodecadienyl.

In formula (VII), W may represent a monovalent radical chosen from the group consisting of an alkyl group having 1 to 8 carbon atoms, which is optionally substituted with at least one halogen atom, and an aryl group. W may advantageously represent a monovalent radical chosen from the group consisting of methyl, ethyl, propyl, 3,3,3-trifluoropropyl, xylyl, tolyl and phenyl.

Preferably, said bifunctional compound is a polyorganosiloxane comprising at least two units of formula (I) or more, and at least two units of formula (V) or more.

The bifunctional polyorganosiloxane may have a linear, branched, cyclic or network structure.

When it is a question of linear polyorganosiloxanes, they may essentially consist:
of siloxyl units "D" chosen from units of formulae $HZSiO_{2/2}$, $Y_2SiO_{2/2}$, $YLSiO_{2/2}$ and $W_2SiO_{2/2}$;
of siloxyl units "M" chosen from units of formulae $HZ_2SiO_{1/2}$, $Y_3SiO_{1/2}$, $Y_2LSiO_{1/2}$, $YL_2SiO_{1/2}$ and $W_3SiO_{2/2}$.

By way of examples of units "D", mention may be made of dimethylsiloxy, hydromethylsiloxy, methylphenylsiloxy, methylvinylsiloxy, methylbutenylsiloxy, methylhexenylsiloxy, methyldecenylsiloxy and methyldecadienylsiloxy groups.

By way of examples of units "M", mention may be made of trimethylsiloxy, dimethylhydrosiloxy, dimethylphenylsiloxy, dimethylvinylsiloxy and dimethylhexenylsiloxy groups.

These linear polyorganosiloxanes may be oils having a dynamic viscosity at 25° C. of between 1 mPa·s and 100 000 mPa·s, preferentially between 10 mPa·s and 5000 mPa·s, or gums having a dynamic viscosity at 25° C. greater than 100 000 mPa·s.

When it is a question of cyclic polyorganosiloxanes, they may consist of siloxyl units "D" chosen from units of formulae $HZSiO_{2/2}$, $Y_2SiO_{2/2}$, $YLSiO_{2/2}$ and $W_2SiO_{2/2}$. Examples of such units "D" are described above. These cyclic polyorganosiloxanes may have a dynamic viscosity at 25° C. of between 1 mPa·s and 5000 mPa·s.

The dynamic viscosity at 25° C. of all the polymers described in the present application can be measured using a Brookfield viscometer, according to standard AFNOR NFT 76 102 of February 1972.

Examples of polyorganosiloxanes which may be bifunctional compounds are:

dimethylhydromethylvinylmethylpolysiloxanes comprising dimethylvinylsilyl ends;
dimethylhydromethylvinylmethylpolysiloxanes comprising dimethylhydrosilyl ends;
dimethylhydromethylvinylmethylpolysiloxanes comprising dimethylvinylsilyl ends;
dimethylhydromethylpropylglycidyl ether methylpolysiloxanes comprising trimethylsilyl ends.

In what follows, when it is a question of the use of the unsaturated compound (B) and of the siloxane compound (A), those skilled in the art will understand that the use of a bifunctional compound is also intended.

In the hydrosilylation process according to the invention, the photocatalyst chosen from polyoxometalates catalyzes the reaction of the unsaturated compound (B) with the siloxane compound (A).

From an implementation point of view, this process comprises at least one step consisting in bringing the unsaturated compound (B) into contact with the siloxane compound (A), in the presence of the catalyst. The bringing of these three elements into contact can be carried out according to conventional techniques known to those skilled in the art.

The process according to the invention can be carried out in a solvent. Appropriate solvents are those which are miscible with the unsaturated compound (B) and with the siloxane compound (A). Examples of particular solvents are aliphatic hydrocarbons, for example pentane, hexane, heptane, pentamethylheptane and petroleum distillation fractions, aromatic hydrocarbons, for example benzene, toluene and ortho-, para- or meta-xylene, halogenated aliphatic or aromatic hydrocarbons, for example tetrachloroethylene, and ethers, for example tetrahydrofuran and dioxane. Alternatively, in the case where the unsaturated compound (B) or the siloxane compound (A) is in liquid form at the temperature of the hydrosilylation reaction, it may be envisioned to use this compound as reaction solvent. The reaction medium may then advantageously be solvent-free.

The unsaturated compound (B), the siloxane compound (A) and the catalyst may be brought into contact in the same phase, then forming a homogeneous reaction medium, or else may be in different phases.

According to a first embodiment, the hydrosilylation process according to the invention is carried out in homogenous solution. The reagents, i.e. the unsaturated compound (B) and the siloxane compound (A), and the photocatalyst may be dissolved in a solvent suitably chosen so as to dissolve all the compounds. This solvent is preferably an organic solvent or a mixture of several organic solvents. This solvent may be chosen from the group consisting of acetonitrile, dichloroethane, nitromethane, 2-methyltetrahydrofuran, dimethylformamide, dimethyl sulfoxide, N-methylpyrrolidone and mixtures thereof. The solvent is preferably chosen from acetonitrile and mixtures of acetonitrile and of another or several other organic cosolvent(s). The organic cosolvent(s) may be chosen from toluene, dichloromethane and tetrahydrofuran. When one or more cosolvent(s) is (are) used as a mixture with acetonitrile, the volume ratio of the cosolvent(s) relative to the acetonitrile is preferably between 1:10 and 6:1, and more preferably between 3:1 and 4:1. The use of acetonitrile alone as reaction solvent has the advantage of obtaining a perfectly homogeneous reaction medium. However, since acetonitrile is expensive, the use of a cosolvent with acetonitrile may also be considered to be advantageous since it makes it possible to reduce the volume of acetonitrile required, and thus to reduce costs.

According to a second embodiment, the hydrosilylation process is carried out by heterogeneous catalysis. In this embodiment, the reagents, i.e. the unsaturated compound (B) and the siloxane compound (A), may be dissolved in a solvent suitably chosen in order to dissolve these reagents, but not the photocatalyst. Said photocatalyst may remain in solid form. Heterogeneous catalysis is particularly advantageous since it allows easy separation of the catalyst from the reagents and reaction products, and easy recycling of the catalyst. The solvent of the reaction phase is preferably an organic solvent or a mixture of several organic solvents. The solvent is preferably toluene.

In this second embodiment of the hydrosilylation process by heterogeneous catalysis, the photocatalyst according to the invention may optionally be introduced into a dispersant solid medium. Various techniques are known to those skilled in the art. For example, the photocatalyst may be impregnated onto a solid support, immobilized in a silica network, attached to a prefunctionalized silica, attached to an ion exchange resin or attached in a polymer membrane.

Whether the reaction is carried out by homogeneous catalysis or heterogeneous catalysis, the catalyst according to the invention is introduced into the reaction medium at a concentration preferably of between 0.01% and 50%, more preferably between 0.05% and 5%, and even more preferably between 1% and 2%, the catalyst concentration being expressed as mole percentage of catalyst relative to the reagent in deficit in the hydrosilylation reaction, which may be the siloxane reagent (A) or the unsaturated reagent (B).

According to the reaction equations (1) and (2) above, the stoichiometric ratio of the hydrosilylation reaction is 1 mol of siloxane compound (A) for 1 mol of unsaturated compound (B). However, this stoichiometric ratio can vary in cases where the siloxane compound (A) and/or the unsaturated compound (B) comprise more than one reactive function. In the process according to the invention, the mole ratio of the Si—H functions of the siloxane compounds (A) to the alkene and alkyne functions of the unsaturated compounds (B) is preferably between 1:100 and 100:1. The choice of this mole ratio can make it possible to control the progression of the hydrosilylation reaction.

When the mole ratio of the Si—H functions of the siloxane compounds (A) to the alkene and alkyne functions of the unsaturated compounds (B) is strictly less than 1, Si—H functions are in deficit relative to the unsaturated functions. If the hydrosilylation reaction is total, the product of the reaction should no longer contain Si—H functions. When the hydrosilylation reaction is carried out between a polyorganosiloxane comprising at least one unit of formula (I) and a non-polymeric unsaturated organic compound as described above, reference can be made to total functionalization of the polyorganosiloxane.

In the opposite case, when the mole ratio of the Si—H functions of the siloxane compounds (A) to the alkene and alkyne functions of the unsaturated compounds (B) is strictly greater than 1, the Si—H functions are in excess relative to the unsaturated functions. The product of the reaction should then still contain Si—H functions. When the hydrosilylation reaction is carried out between a polyorganosiloxane comprising at least one unit of formula (I) and a non-polymeric unsaturated organic compound as described above, reference can be made to partial functionalization of the polyorganosiloxane.

Such partial functionalization reactions are advantageous from the industrial point of view since they result in the preparation of polyorganosiloxane compounds comprising both siloxy units having a hydrogen atom bonded to a silicon atom and siloxy units functionalized with organic substituents of interest, for example dimethylvinylmethylhydromethylpolysiloxanes.

As it happens, currently, the preparation of such compounds by hydrosilylation catalyzed with conventional platinum catalysts is problematic. When the hydrosilylation reaction is finished and when the reaction medium is left in air, the platinum present in the reaction medium can catalyze side reactions. These are in particular dehydrocondensation reactions between Si—H units and the water from the air. This reaction is responsible for gelling of the surface of the reaction medium and is accompanied by release of dihydrogen $H_2$ with the risks of explosion which ensue therefrom. The composition obtained can therefore be stored only with difficulty. It is currently very difficult to withdraw from the reaction medium all traces of platinum catalyst after the hydrosilylation reaction since, even if the reaction is carried out with heterogeneous catalysts, the latter generally release platinum in the homogeneous phase into the reaction media.

In this context, the use of a photocatalyst of POM type as in the hydrosilylation process according to the present invention may advantageously make it possible to solve this side-reaction problem of the prior art. This is because the photocatalyst is active only when it is irradiated. By stopping the irradiation, any parasitic side reaction is prevented. The compositions obtained by partial functionalization by means of the hydrosilylation reaction according to the present invention are advantageously more stable with respect to the storage and safer from an industrial risk point of view. The degree of functionalization can also be very easily controlled.

In addition, the reaction medium may optionally be degassed, so as to be devoid of oxygen. The optional degassing step may make it possible to improve the reaction kinetics, in particular in cases where the reagents are air-sensitive compounds.

In order to promote the hydrosilylation reaction, the photocatalyst according to the invention must be excited using a light source. The process according to the invention preferably comprises at least one step consisting in irradiating the photocatalyst with UV or visible light. This irradiation can be carried out using any existing device which delivers light at the desired wavelength. It may conventionally be an incandescent lamp, an LED lamp, a discharge lamp, in particular a mercury and xenon discharge lamp, or a fluorescent lamp. It may also be a laser source. The irradiation is preferably carried out at a wavelength of between 300 nm and 500 nm, more preferably between 300 nm and 420 nm, and even more preferably between 350 nm and 400 nm. The energy of the irradiation is preferably between 1 $mW/cm^2$ and 5 $W/cm^2$, more preferably between 1 $mW/cm^2$ and 200 $mW/cm^2$, and even more preferably between 10 $mW/cm^2$ and 100 $mW/cm^2$.

According to one embodiment, the irradiation may be kept constant throughout the duration of the hydrosilylation reaction. According to one alternative embodiment, the irradiation may be modified or interrupted during the hydrosilylation reaction. According to another alternative embodiment, the irradiation may be broken up, which means that the irradiation follows a start/stop cycle, according to a constant or variable frequency.

The hydrosilylation process can be carried out at a temperature between 0° C. and 150° C., preferably between 10° C. and 30° C., and more preferably at ambient temperature. For the measurement of the temperature of the hydrosilylation reaction in the present invention, the heating which may possibly be produced by the irradiation source is not taken into account. This process is advantageously carried out at atmospheric pressure, but it can be envisioned to carry out this process at underpressure, for example between 0.01 MPa (100 mbar) and 0.08 MPa (800 mbar), or at overpressure, for example between 0.1 MPa (1 bar) and 8 MPa (80 bar).

The hydrosilylation process according to the invention may be a batch process. The reaction may be carried out for a period which varies according to the reagents involved, the catalyst used and the reaction conditions, in particular according to the concentrations of reagents and of catalyst. Generally, the reaction time may be between 1 minute and 24 hours, preferably between 30 minutes and 8 hours, and even more preferably between 1 hour and 4 hours.

However, it is also envisioned to carry out the process according to the invention continuously. According to this embodiment, the reagents are introduced into the reactor in the form of one or more continuous streams. The photocatalyst may, for its part, also circulate in a continuous stream in the reactor, in particular if the process is carried out in a homogeneous solution. In the case of a heterogeneous catalyst, it may be fixed inside the reactor, for example in the form of a fixed catalytic bed or of a mobile catalytic bed. When the process according to the invention is a continuous process, the flow rate of the streams circulating in the reactor may be fixed by those skilled in the art according to the volume of the reactor so as to ensure a residence time of the reagents sufficient, in the presence of the photocatalyst, for the hydrosilylation reaction to be carried out.

The inventors have discovered that, advantageously, the use of the photocatalyst according to the invention makes it possible to perform hydrosilylation reactions under operating conditions that are easy to implement, without compounds that are particularly dangerous or expensive, with degrees of conversion that are entirely satisfactory. The degrees of conversions of siloxane reagent (A) and/or of unsaturated reagent (B) may advantageously be greater than 50%, or even 60%, or even 75%, or even 80%, or even 90%, and preferably between 90% and 100%.

In the present application, the terms "degree of conversion" and "degree of transformation", abbreviated to DC, are synonymous and denote, for each reagent, as a percentage, the initial number of moles of Si—H functions of the siloxane reagent (A) or of alkene and alkyne functions of the unsaturated reagent (B), minus the number of moles of these functions remaining after reaction, divided by the initial number of moles of these functions.

The products obtained by means of the process according to the invention may optionally, during a subsequent step, be purified using the conventional means well known to those skilled in the art. The products may, for example, be purified by flash chromatography on silica gel.

A subject of the present invention is also a means specially designed for the implementation of the hydrosilylation process described above. This means consists of a composition comprising:
  a siloxane compound (A) comprising at least one hydrogen atom bonded to a silicon atom,
  an unsaturated compound (B) comprising at least one alkene function and/or at least one alkyne function, and
  a photocatalyst chosen from polyoxometalates.

This composition forms the reaction medium in which the photocatalyzed hydrosilylation reaction according to the invention can take place. To do this, this composition can be irradiated as described above, which will have the effect of activating the photocatalyst and will allow the reaction between the unsaturated compound (B) and the siloxane compound (A).

Preferably, the unsaturated compound (B), the siloxane compound (A) and the photocatalyst are as described above in the present application.

According to a first embodiment, the composition according to the invention may be a solution. In this case, the hydrosilylation process may take place in a homogeneous solution. The composition preferably comprises a solvent which may be chosen as described above in the case of a hydrosilylation process in a homogeneous solution.

According to a second embodiment, the composition according to the invention may be a suspension. Preferably, the unsaturated compound (B) and the siloxane compound (A) form a homogeneous reaction medium in a solvent in which the photocatalyst is not soluble. In this case, the hydrosilylation process may be a process by heterogeneous catalysis. The composition preferably comprises a solvent which may be chosen as described above in the case of a hydrosilylation process by heterogeneous catalysis. The photocatalyst may optionally be introduced into a dispersant solid medium, as previously described.

The concentration of photocatalyst in the composition according to the invention is preferably between 0.01% and 50%, more preferably between 0.05% and 5%, and even more preferably between 1% and 2%, the concentration of catalyst being expressed as mole percentage of catalyst relative to the reagent which is in deficit in the hydrosilylation reaction, which may be the siloxane reagent (A) or the unsaturated reagent (B).

In addition, the mole ratio of the Si—H functions of the siloxane compounds (A) to the alkene and alkyne functions of the unsaturated compounds (B) is preferably between 1:100 and 100:1. According to one embodiment, the mole ratio of the Si—H functions of the siloxane compounds (A) to the alkene and alkyne functions of the unsaturated compounds (B) is strictly less than 1. The Si—H functions are in deficit relative to the unsaturated functions. According to another embodiment, the mole ratio of the Si—H functions of the siloxane compounds (A) to the alkene and alkyne functions of the unsaturated compounds (B) is strictly greater than 1. The Si—H functions are then in excess relative to the unsaturated functions.

The composition according to the invention may optionally comprise additives. These additives may in particular be chosen from photosensitizers. Photosensitizers which may be used as additives in the present invention are described in patent documents EP 1 133 971 and EP 1 745 083. The photosensitizers are preferentially chosen from the group consisting of ketones, in particular aromatic ketones, coumarin dyes, xanthene dyes, xanthones, thioxanthones, acridine dyes, thiazole dyes, thiazine dyes, oxazine dyes, azine dyes, aminoketone dyes, porphyrins, polycyclic aromatic hydrocarbons such as naphthalenes, anthracenes, phenanthrene, pyrenes, fluorenes, fluoranthenes and chrisenes, ketone compounds substituted in the para-position with an aminostyryl group, aminotriarylmethanes, merocyanines, squarylium dyes and pyridium dyes. The photosensitizers of ketone type which are particularly preferred are camphorquinone, benzophenone and thioxanthone. The composition according to the invention may also comprise, as additive, electron-donating compounds, such as, for example, those described in patent document EP 1 133 971. However, the concentration of additive in the composition according to the invention is advantageously less than 1000 ppm by weight relative to the total weight of the composition, and more preferably between 0 and 300 ppm.

EXAMPLES

Synthesis of Tetrabutylammonium Decatungstate (TBADT)

Tetrabutylammonium bromide (10.7 g) and sodium tungstate dihydrate (22.2 g) were dissolved separately in 600 ml of water in two Erlenmeyer flasks and brought to 90° C. with vigorous stirring. The pH of each solution was adjusted to 2, in a controlled manner, by dropwise addition of concentrated hydrochloric acid (the sodium tungstate solution then becomes slightly green in color). The two solutions were then mixed and kept at 90° C. for 1 hour 30 minutes. A white suspension of TBADT formed, and was left to cool to ambient temperature and then filtered on sintered glass (porosity No. 4). The solid was washed with water and oven-dried at 110° C. overnight. After a return to ambient temperature, the white solid was ground with a mortar so as to produce TBADT (20.3 g, 91%) having the appearance of a fine white powder. The purity was evaluated at more than 80% by UV spectrometry ($\epsilon_{323}=1.35\times10^4$ $dm^3 \cdot mol^{-1} \cdot cm^{-1}$ in acetonitrile).

The absorption spectrum of the TBADT synthesized was obtained in acetonitrile using the Jasco V530 UV-visible spectrometer. The absorption spectrum is reproduced in FIG. 1.

Example 1

Hydrosilylation of Ethyl Acrylate with a Siloxane in Acetonitrile

TBADT (10 mol %), 1,1,1,3,5,5,5-heptamethyltrisiloxane (1.5 equiv.) of formula (VIII):

acetonitrile which is dry and degassed (by three successive freezing/vacuum/melting cycles) and ethyl acrylate (1 equiv.) were successively placed in a round-bottomed flask equipped with a magnetic bar, with an argon or nitrogen inlet and with a septum.

The reaction medium was irradiated with a UV lamp (Omnicure series 1000) emitting in the UV range at 365 nm, at an energy equal to 20% of the maximum energy of the lamp of 270 mW/cm² for 3 hours. Once the reaction was complete, the solvents were evaporated off under reduced pressure. The proton NMR of the reaction crude makes it possible to estimate the degree of conversion. The reaction crude was then purified by flash chromatography on silica gel.

The degree of conversion and the relative yield of the reaction were measured by 1H NMR analysis at 300 MHz.

The compound of formula (XI):

was obtained with a degree of conversion of 84% and a yield of 10%.

The yield denotes here, as a percentage, the number of moles of product (IX) obtained after reaction, divided by the initial number of moles of ethyl acrylate.

The invention claimed is:

1. A process for hydrosilylation between a siloxane compound (A) comprising at least one hydrogen atom bonded to a silicon atom and an unsaturated compound (B) comprising at least one alkene function and/or at least one alkyne function, wherein said process is catalyzed by a photocatalyst chosen from polyoxometalates.

2. The process as claimed in claim 1, wherein said photocatalyst is a decatungstate.

3. The process as claimed in claim 1 wherein said siloxane compound (A) is a polyorganosiloxane comprising at least one unit of formula (I):

$$H_d Z_e SiO_{(4-(d+e))/2} \qquad (I)$$

in which:
Z represents a monovalent radical other than a hydrogen atom,
d and e represent integers, d being 1 or 2, e being 0, 1 or 2 and (d+e) being 1, 2 or 3;
and optionally other units of formula (II):

$$Z_f SiO_{(4-f)/2} \qquad (II)$$

in which:
Z has the same meaning as above, and
f represents an integer between 0 and 3.

4. The process as claimed in claim 3, wherein, in formula (I), the symbol d is 1 and Z represents a monovalent radical chosen from the group consisting of an alkyl group having 1 to 8 carbon atoms, which is optionally substituted with at least one halogen atom, and an aryl group.

5. The process as claimed in claim 1, wherein said unsaturated compound (B) comprises one or more alkene functions and/or one or more alkyne functions, and from 2 to 40 carbon atoms.

6. The process as claimed in claim 1, wherein said unsaturated compound (B) is chosen from the group consisting of:
non-polymeric unsaturated organic compounds,
polyorganosiloxane compounds comprising at least one alkene function and/or at least one alkyne function,
and mixtures thereof.

7. The process as claimed in claim 6, wherein said unsaturated compound (B) is a non-polymeric unsaturated organic compound chosen from the group consisting of:
acetylene;
$C_1$ to $C_4$ alkyl acrylates and methacrylates;

acrylic or methacrylic acid;
alkenes, optionally octene and optionally 1-octene;
allyl alcohol;
allylamine;
allyl glycidyl ether;
piperidine allyl ether, optionally sterically hindered piperidine allyl ether;
styrenes, preferentially alpha-methylstyrene,
1,2-epoxy-4-vinylcyclohexane,
allyl chloride;
chloroalkenes, optionally allyl chloride; and
fluoroalkenes, optionally 4,4,5,5,6,6,7,7,7-nonafluoro-1-heptene.

8. The process as claimed in claim 6, wherein said unsaturated compound (B) is chosen from polyorganosiloxane compounds comprising at least one unit of formula (V):

$$Y_g L_h SiO_{(4-(g+h))/2} \qquad (V)$$

in which:
Y represents a linear or branched radical containing between 2 and 12 carbon atoms, having at least one alkene function and/or at least one alkyne function, and optionally at least one heteroatom;
L represents a monovalent radical not comprising an alkene or alkyne function;
g and h represent integers, g being 1, 2 or 3, h being 0, 1 or 2 and (g+h) being 1, 2 or 3;
and optionally comprising other units of formula (VI):

$$L_i SiO_{(4-i)/2} \qquad (VI)$$

in which:
L has the same meaning as above, and
i represents an integer between 0 and 3.

9. The process as claimed in claim 1, wherein the siloxane compound (A) comprising at least one hydrogen atom bonded to a silicon atom and the unsaturated compound (B) comprising at least one alkene function and/or at least one alkyne function are one and the same bifunctional compound.

10. The process as claimed in claim 9, wherein said bifunctional compound is a polyorganosiloxane comprising at least one unit of formula (I):

$$H_d Z_e SiO_{(4-(d+e))/2} \qquad (I)$$

in which:
Z represents a monovalent radical other than a hydrogen atom;
d and e represent integers, d being 1 or 2, e being 0, 1 or 2 and (d+e) being 1, 2 or 3;
and at least one unit of formula (V):

$$Y_g L_h SiO_{(4-(g+h))/2} \qquad (V)$$

in which:
Y represents a linear or branched radical containing between 2 and 12 carbon atoms, having at least one alkene function and/or at least one alkyne function, and optionally at least one heteroatom;
L represents a monovalent radical not comprising an alkene or alkyne function;
g and h represent integers, g being 1, 2 or 3, h being 0, 1 or 2 and (g+h) being 1, 2 or 3;
and optionally other units of formula (VII):

$$W_j SiO_{(4-j)/2} \qquad (VII)$$

in which:
W represents a monovalent radical other than a hydrogen atom and not comprising an alkene or alkyne function, and
j represents an integer between 0 and 3.

11. The process as claimed in claim 1, which comprises irradiating the photocatalyst with UV or visible light, the wavelength of which is between 300 nm and 500 nm.

12. The process as claimed in claim 1, which is carried out in a homogeneous solution.

13. The process as claimed in claim 1, which is carried out by heterogeneous catalysis.

14. A composition comprising:
a siloxane compound (A) comprising at least one hydrogen atom bonded to a silicon atom,
an unsaturated compound (B) comprising at least one alkene function and/or at least one alkyne function, and
a photocatalyst chosen from polyoxometalates.

15. The composition of claim 14, wherein said photocatalyst is a decatungstate.

16. The composition of claim 14, wherein said photocatalyst is tetrabutylammonium decatungstate.

17. The process of claim 1, wherein said photocatalyst is tetrabutylammonium decatungstate.

18. A product formed by the irradiation of a composition of claim 14, with UV or visible light, the wavelength of which is between 300 nm and 500 nm.

19. The composition of claim 4, comprising 0.05 to 5% of the photocatalyst.

* * * * *